(12) United States Patent
Cardwell et al.

(10) Patent No.: US 6,423,076 B1
(45) Date of Patent: Jul. 23, 2002

(54) LASER DIRECTED PORTABLE MRI STEREOTACTIC SYSTEM

(75) Inventors: David M. Cardwell; Steven E. Harms, both of Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 1 day.

(21) Appl. No.: 09/721,023

(22) Filed: Nov. 22, 2000

Related U.S. Application Data (60) Provisional application No. 60/169,472, filed on Dec. 7, 1999.

(51) Int. Cl.[7] .............................................. A61B 19/00
(52) U.S. Cl. ...................................................... 606/130
(58) Field of Search ......................................... 606/130

(56) References Cited

U.S. PATENT DOCUMENTS

| | | | |
|---|---|---|---|
| 4,583,538 A | | 4/1986 | Onik et al. |
| 4,651,732 A | | 3/1987 | Frederick |
| 5,221,283 A | | 6/1993 | Chang |
| 5,437,280 A | | 8/1995 | Hussman |
| 5,590,655 A | | 1/1997 | Hussman |
| 5,598,269 A | | 1/1997 | Kitaevich et al. |
| 6,021,342 A | * | 2/2000 | Brabrand .................... 600/427 |
| 6,044,291 A | | 3/2000 | Rockseisen |
| 6,047,249 A | * | 3/2000 | Regn ........................... 600/429 |
| 6,110,112 A | * | 8/2000 | Heywang-Koebrunner . 600/439 |

* cited by examiner

Primary Examiner—Eduardo C. Robert
(74) Attorney, Agent, or Firm—Ray F. Cox, Jr.

(57) ABSTRACT

A stereotactic device for localizing an MRI-imaged mass using horizontal and vertical protractors on which a laser is mounted. The protractors and laser are mounted on a table which may be positioned horizontally and vertically with respect to the patient table. The portion of the patient's body being imaged is fixed by a compression plate to which a reference target is mounted. The reference target incorporates a substance which is strongly imaged by the MRI. The compression plate comprises an array of relatively large apertures through which the radiologist may guide an instrument. From the MRI images, the radiologist takes an angle between the reference target and the suspect mass from each of two perpendicular planes and inputs these angles into the protractors of the stereotactic device. The table of the stereotactic device is adjusted horizontally or vertically with respect to the patient table so that the beam of the laser aligns with the reference target. The reference target is then removed from the compression plate so that the laser beam illuminates an entry point on the patient's body. The laser beam is thus aligned along a trajectory from the entry point to the suspect mass. The radiologist is then able to simply follow the laser beam with a biopsy needle or other instrument to make consistent arrival at the site of the suspect mass.

5 Claims, 9 Drawing Sheets

LASER DIRECTED PORTABLE MRI STEREOTACTIC SYSTEM

This application claims the benefit of U.S. Provisional Application No. 60/169,472, filed Dec. 7, 1999.

BACKGROUND OF THE INVENTION

The present invention relates to magnetic resonance imaging (MRI), and in particular, to a laser apparatus for guiding surgical procedures based on location information derived from such MRI imaging.

MRI is a technique for imaging structures within a patient's body. An atomic nucleus carries a charge and due to the intrinsic spin associated with the charged nucleus, each nucleus acts like a magnetic dipole. When an external magnetic field is applied to a patient's body, the nuclear dipoles are forced into orientation to the external field. An applied radio frequency pulse at a resonance frequency tilts the nuclei out of alignment. After the pulse passes, the nuclei relax and emit an electromagnetic signal that can be detected by antennas. The detected signal is then analyzed by a Fourier transform technique to yield an image of the internal structure of the patient's body. By manipulating the imposed external magnetic field and the applied radio frequency pulse, the image may be selected to be in a narrow plane. A sequence of such planes provides complete three dimensional information about the internal structure of the portion of the patient's body being imaged. Images may be taken in the coronal plane (the plane that divides the structure into front and back portions), the axial plane (the plane that divides the structure into left and right portions), and the sagittal plane (the plane that divides the structure into upper and lower portions).

If the images of the patient's body show a suspect mass, invasive surgical procedures including biopsy or ablation may be required. Localization of the suspect mass may be performed by the insertion of wires under the guidance of the MRI image. Various techniques are known for guiding an instrument to a suspect mass, e.g., mechanically aligned bores which guide the instrument from a selected entry point to the suspect mass. Such systems are called stereotactic, which means the use of vectors to position an instrument in three-dimensional space.

Such mechanical stereotactic systems are complicated and allow the surgeon little freedom in guiding the instrument. This is a severe limitation in that the skill of the surgeon is often required to precisely locate the suspect mass and insert the instrument into the mass. It is also desirable that a stereotactic system by constructed entirely of non-magnetic material, such as acrylic, aluminum or stainless steel since the system must operate within the fringes of the powerful MRI field. Finally, it is also desirable that a stereotactic system be lightweight, portable and adaptable to various types of MRI devices or to other types of imaging systems. Battery power, for example, would allow a stereotactic system to be independent of the power supply of the; imaging system.

The limitations of the prior art are overcome by the present invention as described below.

SUMMARY OF THE INVENTION

The present invention provides the radiologist performing biopsies and ablations of suspect masses localized by magnetic resonance imaging with a reference to guide needle or fiber insertion into the mass. The invention must be used within the fringe field of the MRI magnet and thus is non-magnetic to prevent the device from being torqued or drawn into the bore of the magnet. Part of the design criterion was that the invention be simple and inexpensive. The invention is able to be adapted to any type of patient table used for delivering a patient to the bore of a MRI magnet or other imaging device. The invention is battery operated and self contained, thus independent of any power requirements of the MRI system.

The stereotactic device of the present invention includes horizontal and vertical protractors on which a laser is mounted. The protractors and laser are mounted on a table which may be positioned horizontally and vertically with respect to the patient table. The portion of the patient's body being imaged, for example, a breast, is fixed by a compression plate to which a reference target is mounted. The reference target incorporates a substance which is strongly imaged by the MRI. The compression plate comprises an array of relatively large apertures through which the radiologist may guide an instrument. It is an important aspect of the present invention that the apertures are not narrow bores limiting the freedom of movement of the instrument. The apertures provide access but are not guides.

From the MRI images, the radiologist takes an angle between the reference target and the suspect mass from each of two perpendicular planes and inputs these angles into the protractors of the stereotactic device which is mounted on the side of the MRI patient table. The table of the stereotactic device is then adjusted horizontally or vertically with respect to the patient table so that the beam of the laser aligns with the reference target. The reference target is then removed from the compression plate so that the laser beam illuminates an entry point on the patient's body. The laser beam is thus aligned along a trajectory from the entry point to the suspect mass. The radiologist is then able to simply follow the laser beam with a biopsy needle or other instrument to make consistent arrival at the site of the suspect mass. The radiologist is able to target multiple pathways from the same entry site or multiple approaches to the target.

The stereotactic device of the present invention is independent of any particular MRI or other imaging system and thus no modifications to an existing system are required. It is desirable that the stereotactic invention be "portable" in the sense that it may be adapted to various types of imaging devices and in operation is independent of any particular imaging device. The invention may however be affixed in a permanent or semi-permanent fashion to a particular imaging device.

MRI images provide excellent localization of masses, but the information is not "real time." Without a guidance system, the only way a radiologist can arrive at the suspect mass with needle insertion is through a hit-and-miss iterative process. The stereotactic device of the present invention provides guidance to the suspect mass and thus saves valuable time and multiple "sticks" to the patient, while allowing the radiologist freedom to adjust the trajectory of the instrument as necessary.

The present invention has been designed for breast biopsies and laser ablation in breasts, but is not so limited and could be used for other areas such as liver or kidney.

The design of presently available MRI coils and the patient table may limit the field of view of the invention. However, these limitations may be overcome by redesigning the coil and patient table.

It is therefore an object of the present invention to provide for a stereotactic system which provides the radiologist performing biopsies and ablations of suspect masses localized by magnetic resonance imaging with a reference to guide instrument insertion into the mass while allowing the radiologist freedom in guiding the instrument.

It is a further object of the present invention to provide for a stereotactic system which is non-magnetic and operable in the fringe field of an MRI magnet.

It is also an object of the present invention to provide for a stereotactic system which is able to be adapted to any type of patient table used for delivering a patient to the bore of a MRI magnet or other imaging device.

It is an additional object of the present invention to provide for a stereotactic system which is battery operated and self contained, thus independent of any power requirements of the MRI or other imaging system.

These and other objects and advantages of the present invention will be apparent from a consideration of the following detailed description of the preferred embodiments in conjunction with the appended drawings as described following.

BRIEF DESCRIPTION OF THE DRAWINGS

FIG. 13b is a partial perspective view of the alternative vertical guide mechanism of FIG. 13a.

DETAILED DESCRIPTION OF THE PREFERRED EMBODIMENTS

Figure 1:
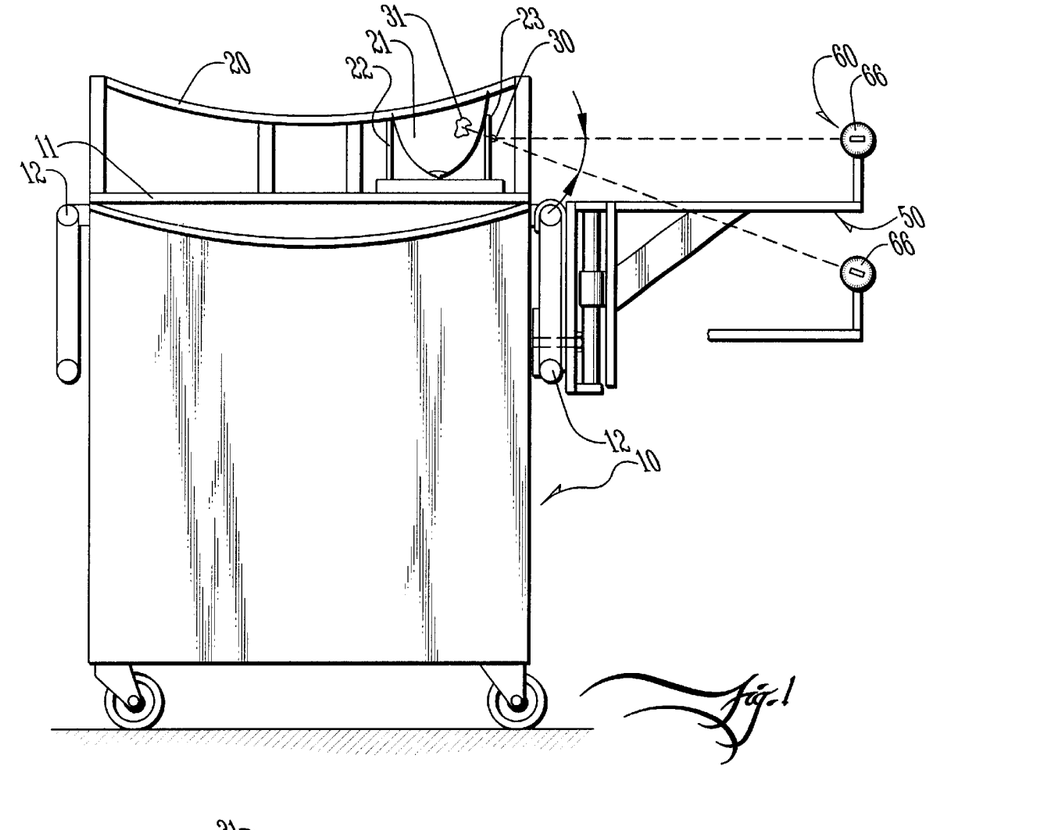
FIG. 1 is a front elevation view of the present invention as installed on an MRI patient table. The patient table is shown with the end of the patient table in section imaging a breast in the axial plane. An alternate position of the present invention is shown in a partial view.
Figure 2:
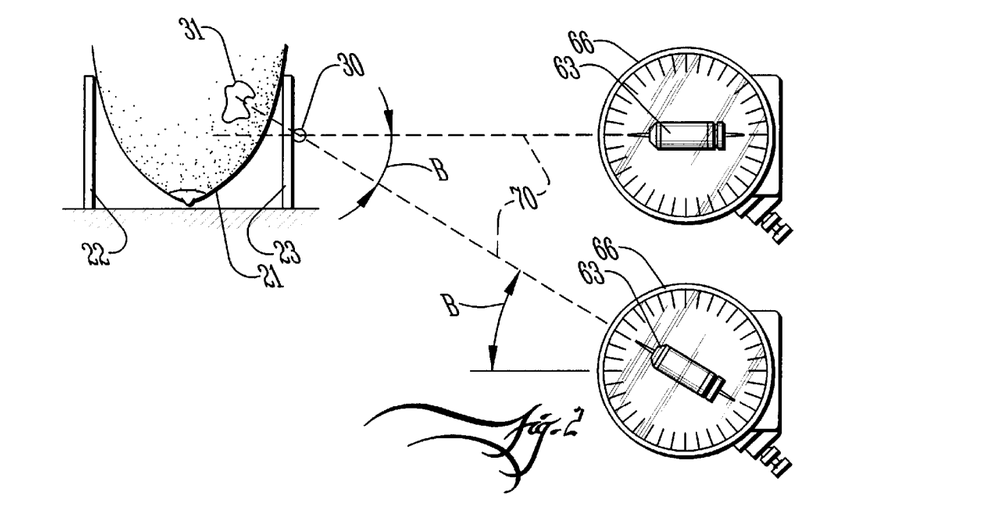
FIG. 2 is a partial enlarged view of the invention shown in FIG. 1
Figure 3:
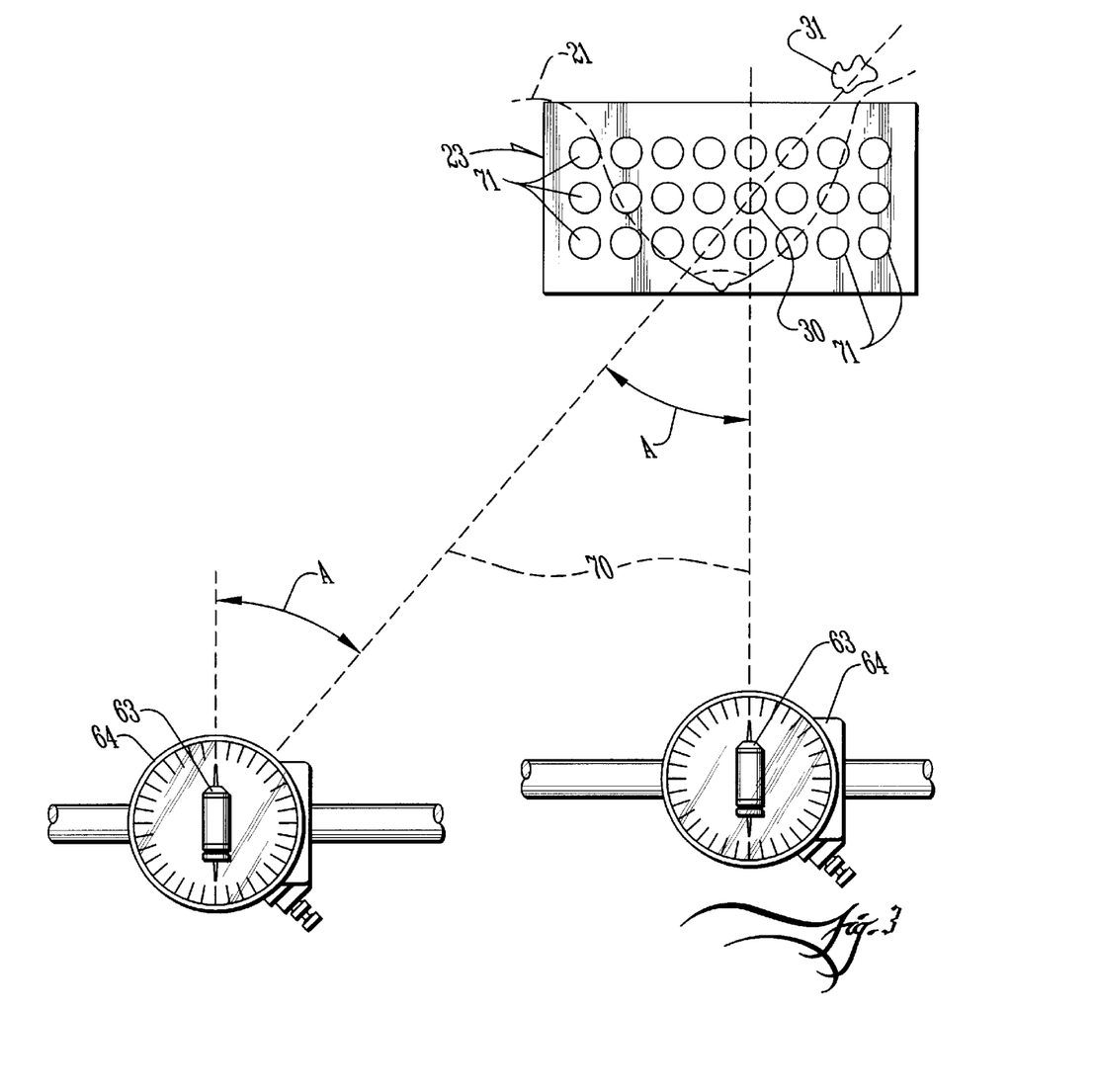
FIG. 3 is a partial top plan view of the breast imaging shown in FIG. 1. The breast is being imaged in the sagittal plane. The partial view of the invention is shown in alternate positions.

With reference to FIGS. 1, 2 and 3, the preferred embodiment of the present invention may be described. A patient is placed on the patient table 10, which comprises a platform 11 axially movable in a horizontal plane. The patient table 10 may be provided with fold-down leaves 12.

The preferred embodiment is described following with reference to the imaging of a breast, however, the present invention is not so limited and the following discussion is intended to be exemplary only. The present invention may be employed in the imaging and localization of other structures of a patient's body.

Figure 9:
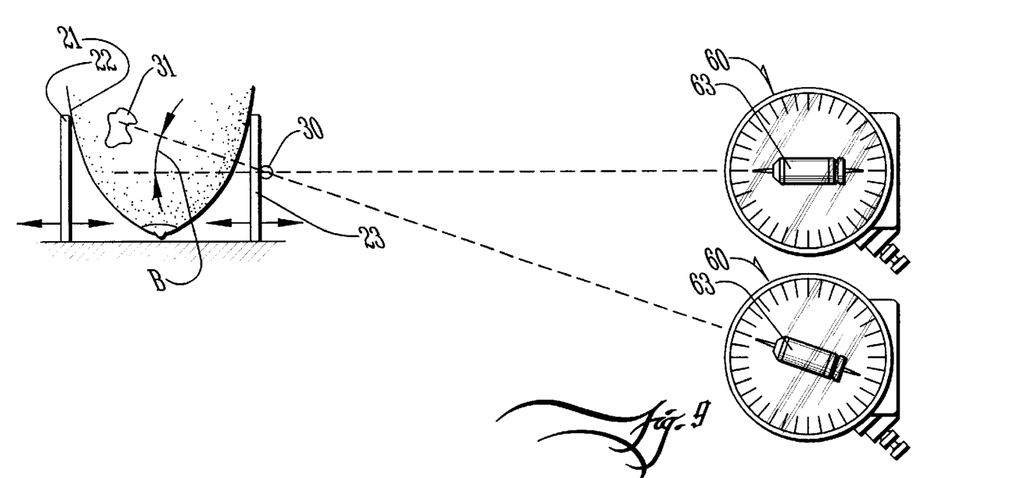
FIG. 9 is similar to FIG. 2 showing schematically by horizontal arrows the movement of the compression plates.

As shown in FIG. 1, the patient is placed on the patient table 10 in proximity to a breast coil 20 so that the breast 21 being imaged is fixed between two compression plates 22, 23. The motion of the compression plates 22, 23 is shown in FIG. 9. As will be described more fully hereinafter, the compression plate 23 is provided with a plurality of apertures. As shown in the partial enlarged view of FIG. 2, a reference target 30 is fixed in one of the apertures of the compression plate 23. It is desirable that the reference target be capable of being plugged into the compression plate for a positive engagement without movement of the reference target. For example, a reference target overlay plate could include a plurality of plugs sized to positively engage a corresponding plurality of apertures on the compression plate. A material capable of being readily imaged would be incorporated into one of the plugs to provide the reference target.

The radiologist uses the MRI image to locate the suspect mass 31. The reference target 30 is also seen on the MRI image. The reference target 30 is any material which is visible on the MRI image. For example, water molecules are selectively imaged by the MRI. Certain substances are well imaged, such as vitamin E (due to the oil content) or copper sulfate solution.

The MRI allows the radiologist to point to the suspect mass 31 and to the reference target 30. The typical MRI instrument has the internal capability to calculate the horizontal angle A in the horizontal plane and the vertical angle B in the vertical plane from the reference target 30 to the suspect mass 31.

Figures 4, 5:
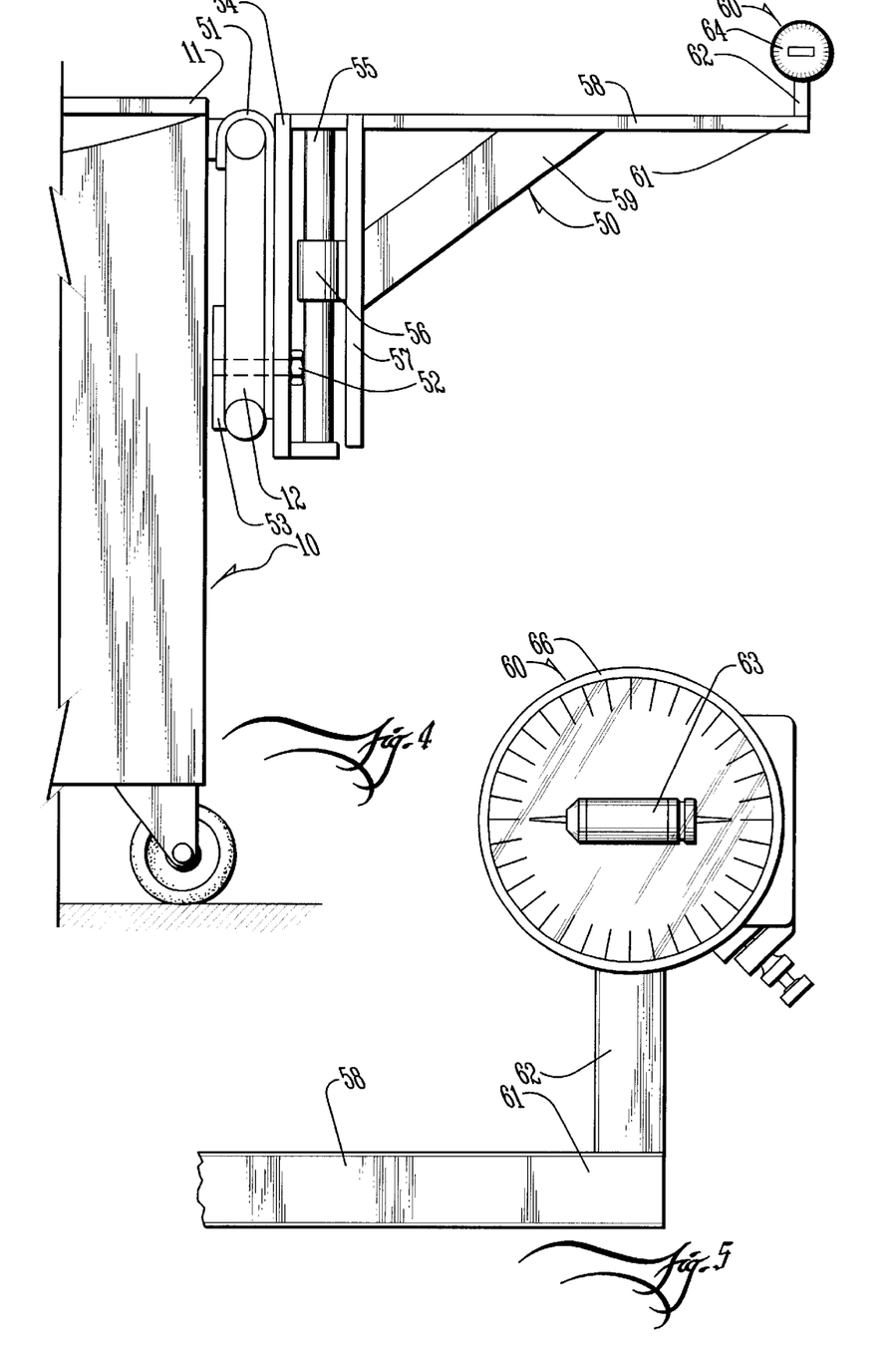
FIG. 4 is a front elevation view of the present invention as installed on an MRI patient table (the patient table is in partial elevation view from the end of the patient table) illustrating an embodiment of the vertical slide.
FIG. 5 is a partial front elevation view of the vertical protractor.

As shown in FIG. 4, the stereotactic assembly 50 includes a hook 51 or other means to attach the stereotactic assembly 50 to the patient platform 11. The patient platform 11 slides axially which allows horizontal adjustment of the position of the patient with respect to the stereotactic assembly 50. In the preferred embodiment, the hook 51 fastens the stereotactic assembly 50 to the fold-down leaf 12. The stereotactic assembly also comprises a fixed vertical member 54 which is rigidly affixed to the hook 51. The stereotactic assembly 50 may be more rigidly affixed to the fold-down leaf 12 by a bolt 52 which.passes through the fixed vertical member 54 and the fold-down leaf 12 and bolts to a clamping plate 53.

In the preferred embodiment, the stereotactic assembly 50 further comprises a vertical tube 55 attached to and spaced outwardly from the fixed vertical member 54. A glide 56 is telescopingly mounted to the vertical tube 55 for vertical movement with respect to the fixed vertical member 54. The stereotactic assembly 50 may also include means for fixing the glide 56 in various adjustable vertical positions with respect to the fixed vertical member 54. The glide 56 is fixed to an adjustable vertical member 57. A table 58 horizontally extends from the adjustable vertical member 57 and is supported by a table support bracket 59. A protractor assembly 60, described more fully below, is affixed to an outboard end 61 of the table 58.

Figure 6:
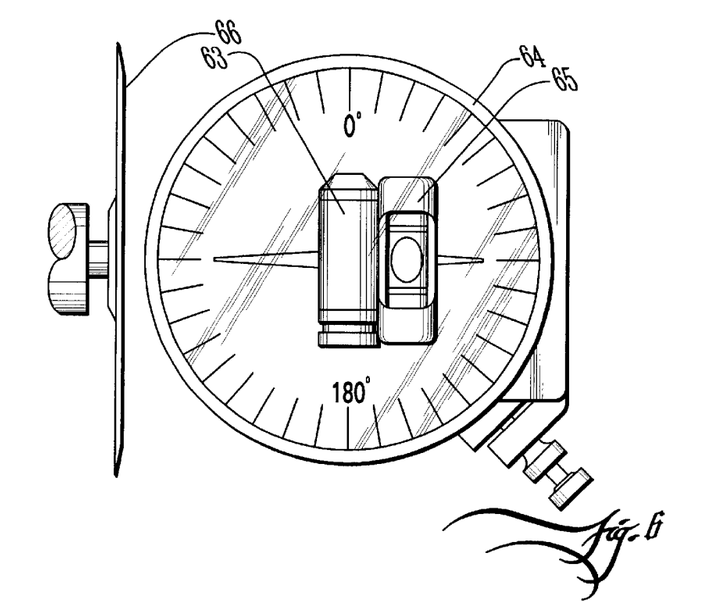
FIG. 6 is a partial top plan view of the horizontal protractor.

The protractor assembly 60 is carried on a vertical support member 62 attached to the outboard end 61 of the table 58. The protractor assembly 60 comprises a battery powered laser 63 as shown in FIGS. 5 and 6 mounted to a horizontal protractor 64. The battery operation is important in that it makes the device independent of the MRI power supply. This allows for portability and compatibility with any MRI or similar device.

The laser 63 is mounted such that the centerline of the horizontal protractor is aligned in a vertical plane with the centerline of the beam of the laser 63. The horizontal protractor 64 is preferably of clear, non-magnetic material, such as acrylic. The horizontal protractor 64 is provided with etched graduations giving angles in the horizontal plane. The horizontal protractor 64 may also be provided with vernier controls to allow for fine adjustment of the angular position of the laser 63 and to positively fix the protractor in position. A simple form of vernier may be provided by a screw acting tangentially on the protractor against the force of a biasing means such as a spring or elastic band. The horizontal protractor 64 is also provided with a bubble level 65 to use in ensuring that the horizontal protractor 64 is level before use. The horizontal protractor 64 is mounted for rotation so that the laser 63 may be pointed to any selected angle in the horizontal plane.

The horizontal protractor 64 is mounted for rotation on a vertical protractor 66 such that the centerline of the laser 63 is passes through a horizontal plane that also includes the center pivot for the vertical protractor 66. The vertical protractor 66 is preferably of a clear, non-magnetic material, such as acrylic. The vertical protractor 66 is provided with etched graduations giving angles in the vertical plane. A vernier adjustment means as described above may be provided for the vertical protractor also. The level 65 can also be used to ensure that the stereotactic assembly 50 is oriented vertically with respect to the patient's platform 11.

Figure 7:
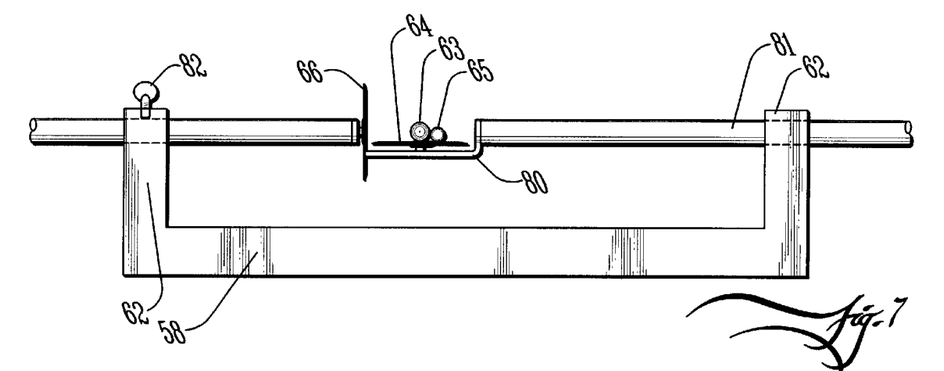
FIG. 7 is a partial side elevation view of an embodiment of the present invention in which the center line of the laser pointer is in a plane which always contains the center line of the vertical pivot.

One embodiment of the present invention is shown in FIG. 7. The horizontal protractor 64 is mounted for rotation on a turntable support 80. The turntable support 80 is affixed to a vertical protractor 66. The vertical protractor 66 and turntable support 80 are affixed to a rod 81 in an offset fashion so that the centerline of the laser 63 is in the same horizontal plane as the center pivot of the vertical protractor 66. The rod 81 is mounted for pivotal rotation on two vertical supports 62 which are attached to the table 58. The rod 81 may be fixed in a particular orientation by a set screw 82. This arrangement allows the orientation of the laser 64 to be fixed in the vertical plane. As an alternative, instead of moving the patient platform to point the laser 63 to the reference target 30, the rod 81 may be moved horizontally with respect to the vertical supports 62.

As noted above, the MRI allows the radiologist to point to the suspect mass 31 and to the reference target 30. The MRI instrument then calculates the horizontal angle A in the horizontal plane and the vertical angle B in the vertical plane from the reference target 30 to the suspect mass 31. In order to localize the suspect mass 31 and to provide the guidance trajectory for the radiologist, the angle A is first set on the horizontal protractor 64 so that the laser 63 is pointed at angle A in the horizontal plane. The patient platform 11 is then moved axially in the horizontal plane until the beam 70 of the laser 63 is pointed at the reference target 30.

Figure 8:
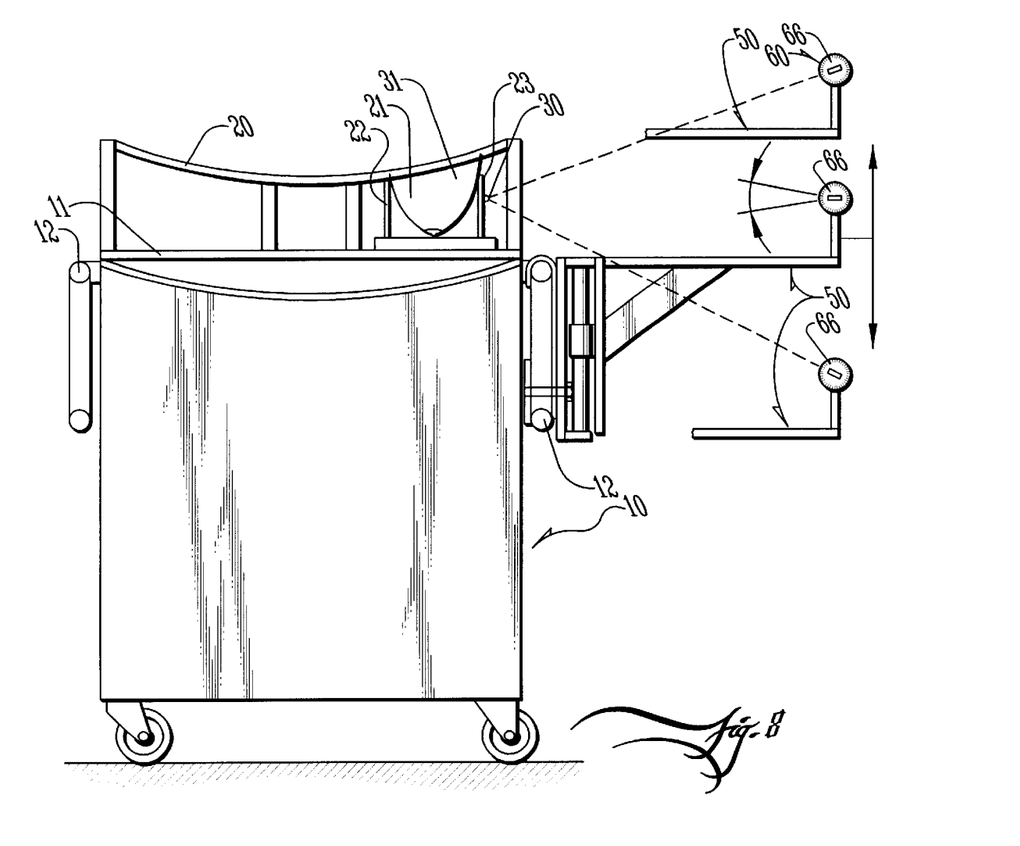
FIG. 8 is a front elevation view of the present invention as installed on an MRI patient table illustrating in alternate views the limits of vertical displacement of the protractors with respect to the imaged object.

Then, with reference to FIG. 2, the angle B is set on the vertical protractor 66 so that the beam 70 of the laser 63 is pointed along the angle B in the vertical plane. The table 58 is then adjusted vertically by moving the glide 56 with respect to the vertical tube 55 until the beam 70 of the laser 63 is once again pointed to the reference target 30. The beam 70 therefore establishes a trajectory from the reference target 30 to the suspect mass 31. The maximum vertical motion of the stereotactic assembly 50 may be limited by the position of the breast coil 20 and the patient table 10 as shown in FIG. 8. However, such limitations may be overcome by a redesign of the coil and table.

After established the trajectory of the guide beam 70, the reference target 30 is then removed from the compression plate 23 so that an entry point on the breast is illuminated by the laser beam 70. By aligning an instrument, such as a biopsy needle, with the laser beam 70, the radiologist is able to guide the instrument from the entry point on the breast 21 to the suspect mass 31. The radiologist is therefore able to see that the needle enters the patient properly yet still has full control of the needle so that the radiologist is able to adjust the motion of the needle as necessary. The insertion of the needle requires the radiologist to exercise tactile skill in locating and inserting the needle into the suspect mass. The radiologist must "feel" for the mass and often must twist the needle to properly insert it into the mass. Prior art stereotactic systems are mechanical in that the needle is inserted into a guide which limits the freedom of motion of the radiologist.

If a breast biopsy is being performed, compression plates 22, 23 are used to fix the breast 21 in position. A commonly-used compression plate is solid with angular edges. The compression plate 23 used with this invention has a number of arrayed apertures 71 as shown in FIG. 3. The apertures 71 are large circular openings with beveled edges and the compression plate 23 has rolled-over edges and rounded edges for greater comfort for the patient. When the compression plates is compressed against the patient's skin, the tissue tends to slightly protrude through the apertures. By beveling the edge of the aperture, the compression plate tends to grip the protruding tissue and provides resistance to slippage of the patient's skin along the surface of the compression plate. In the preferred embodiment, it is desirable to bevel the edge of the aperture from both sides of the compression plate. It is an important aspect of this invention that the aperture be large enough to provide free access to the radiologist. The apertures 71 are not narrow bores for guiding an instrument, they are wide openings that provide free access and allow a wide range of motion to the radiologist in inserting an instrument into the entry point on the patient's body.

As discussed above, the reference target 30 is fixed in the compression plate 23 so as to provide a reference point. The compression plate 23 may also be modified to provide reference information directly on the MRI image. For example, reference numerals, such as coordinates in a three-dimensional coordinate system, may be formed in the compression plate 23 by routing the numeral into the acrylic material of the compression plate 23. The routed areas are then filled with a material that images well, such as copper sulfate solution. The routed areas are then sealed, e.g., with a thin sheet of acrylic. When imaged the acrylic will not be visible on the MRI image, but the copper sulfated reference numerals will be visible. It may be desirable that the reference coordinates or numerals be removable from the compression plate, for example, to allowing for cleaning the compression. In an alternative embodiment, the reference numeral or coordinates may be formed into a separate overlay plate that can be plugged into the compression plate during imaging and removed for subsequent procedures.

Figure 10:
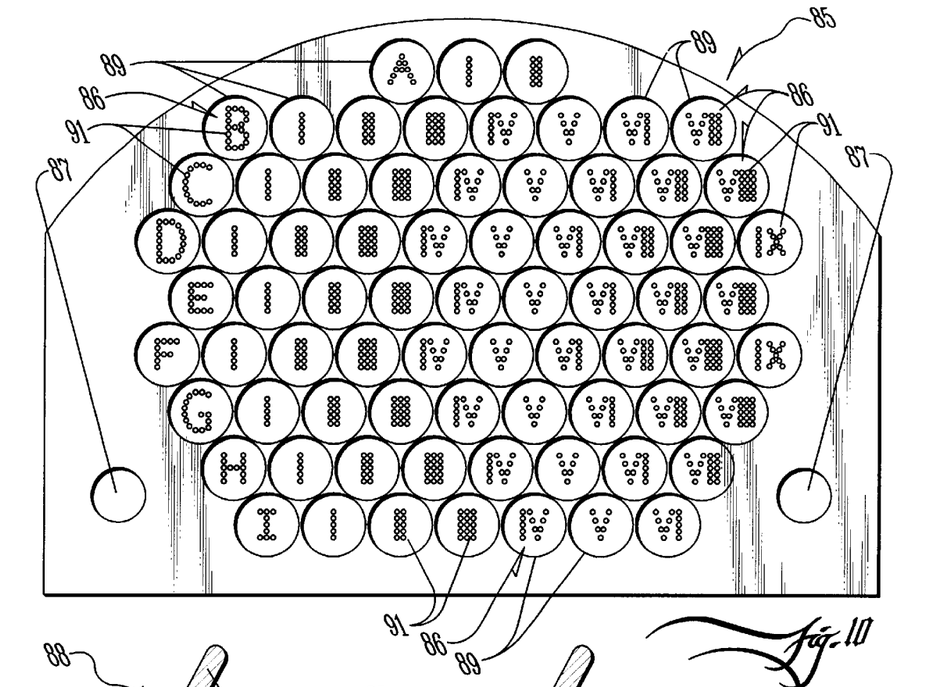
FIG. 10 is a plan view of the reference target overlay plate.
Figure 11A:
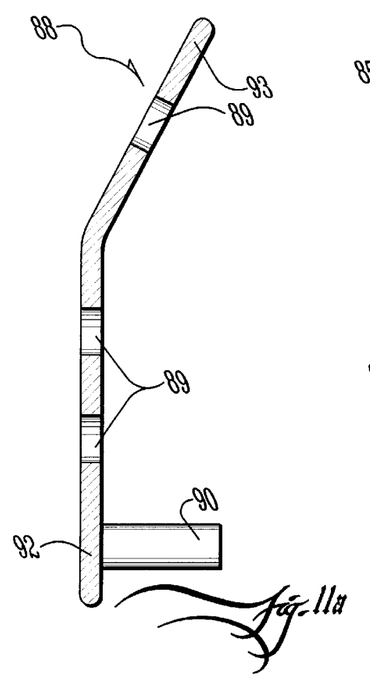
FIG. 11a is a left elevation cross-sectional view of an alternative embodiment of a compression plate.
Figure 11B:
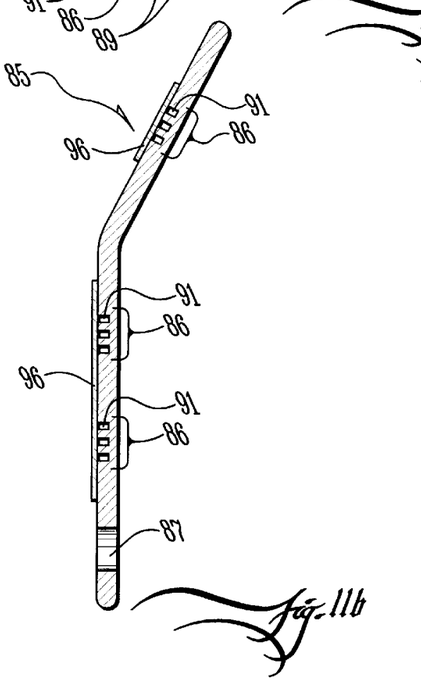
FIG. 11b is a left elevation cross-sectional view of a reference target overlay plate.

The alternative embodiment of a reference target overlay plate is shown in FIG. 10. Reference numerals or targets may be formed in the same manner as described above. The overlay plate 85 includes a plurality of reference targets 86 formed by drilling a series of target holes 91 partly through the overlay plate 85. The target holes 91 are then filled with a material that images well, such as copper sulfate solution. The target holes 91 are then sealed, e.g., with a thin sheet 96 of acrylic. The embodiment of FIGS. 10, 11a and 11b show a series of reference targets 86 which align with corresponding apertures 89 in a compression plate 88. Alignment of the overlay plate 85 with the compression plate 88 may be accomplished by any of a number of means known to those in the art. For example, one or more alignment posts 90 may be provided in the compression plate 88 to align with and connect with the alignment holes 87 in the overlay plate 85. Means may also be provided for releasably connecting the alignment posts 90 to the alignment holes 87.

In some embodiments of the compression plate 88 and the overlay plate 85, the plates 88, 85 may be flat, but embodiments of the plates 88, 85 are contemplated in which the plates 88, 85 are shaped three-dimensionally to more accurately and comfortably conform to the portion of the body being imaged. In the embodiment of FIGS. 11a and 11b, the compression plate 88 is provided with a lower portion 92 which is angled with respect to an upper portion 93. This configuration provides a better arrangement for imaging a breast. Desirably, the upper portion 93 is at an angle of approximately 40° to the lower portion 92. The overlay plate 85 is correspondingy shaped to conform to the shape of the compression plate 88.

Figure 12A:
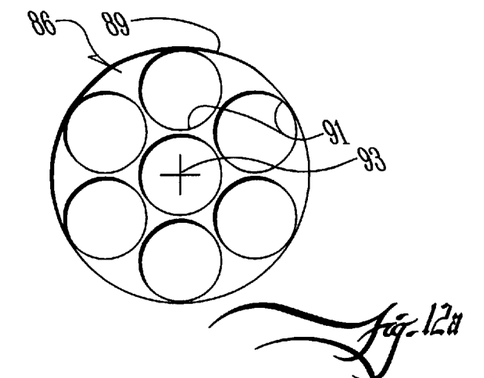
FIGS. 12a, b, and c are plan views of alternative embodiments of reference targets.
Figure 12B:
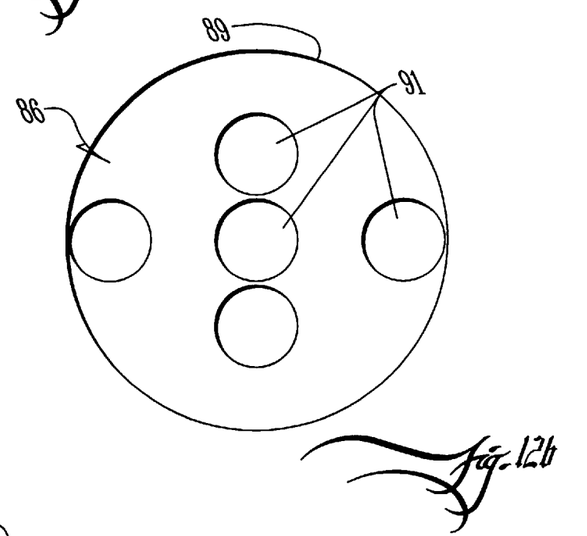
Figure 12C:
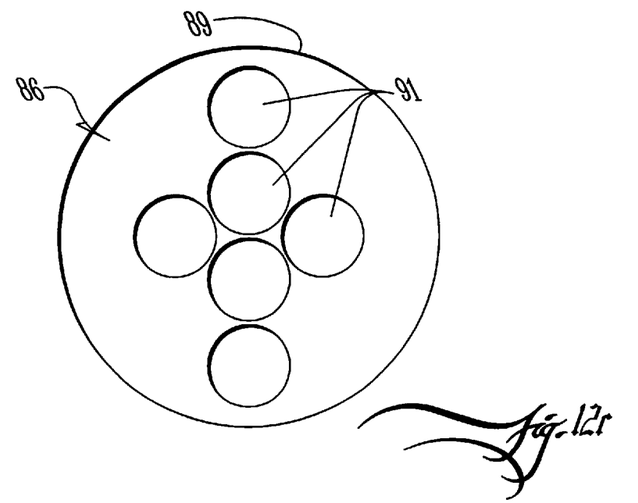

In the embodiment of FIG. 10, the reference targets 86 are identified by letters or numerals to identify a particular aperture 89 in the compression plate 85. Other forms of reference targets 86 are contemplated as being within the scope of the present invention. Examples of reference targets 86 are shown in FIGS. 12a, b, c. FIG. 12a shows a circulation configuration of target holes 91 with a central point 95. FIG. 12b and show alternative arrangements with a linear group of target holes 91 to form a cross-shaped target.

Figure 13A:
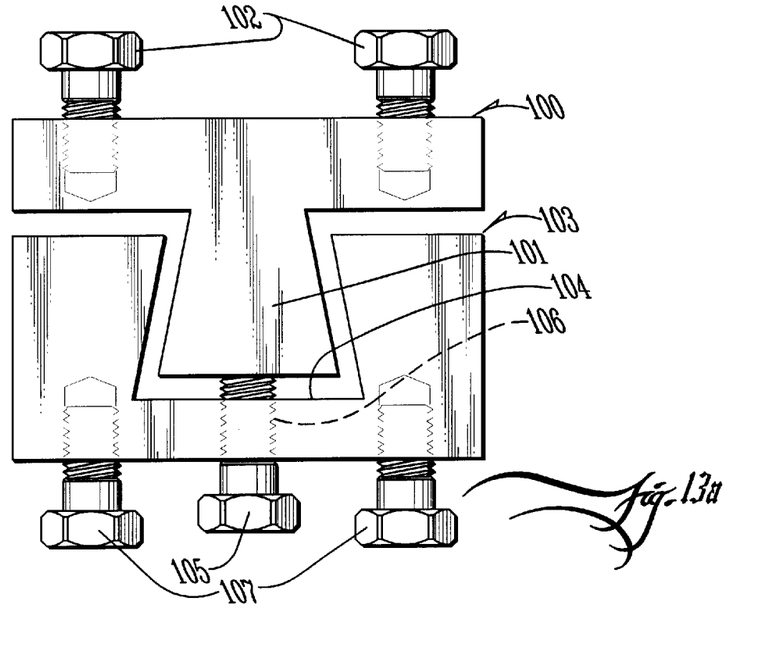
FIG. 13a is an end elevation view of an alternative vertical guide mechanism.
Figure 13B:
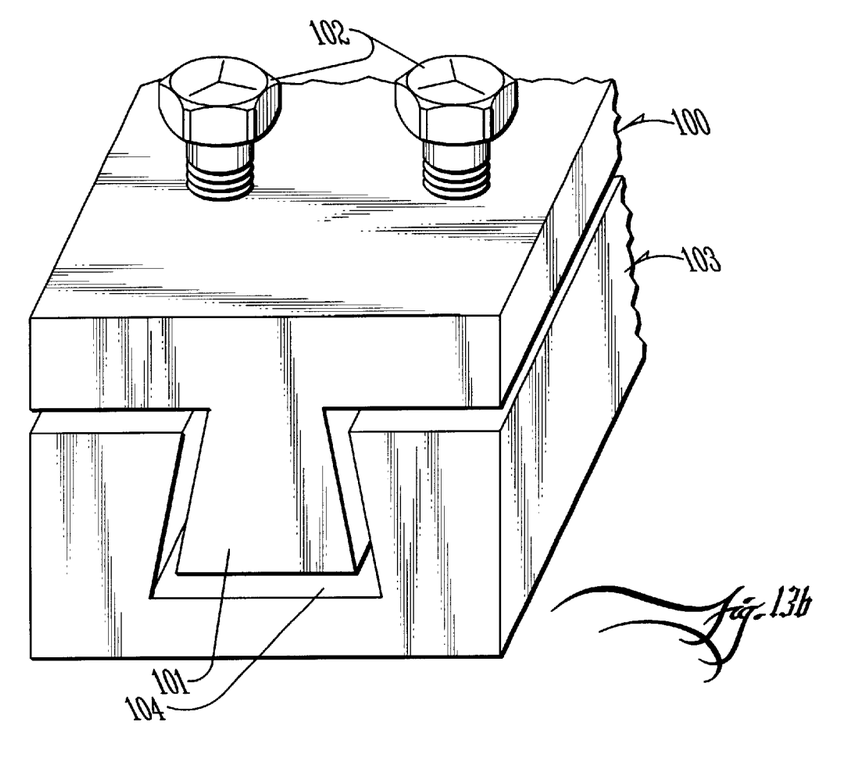
Figures 14A, 14B, 14C:
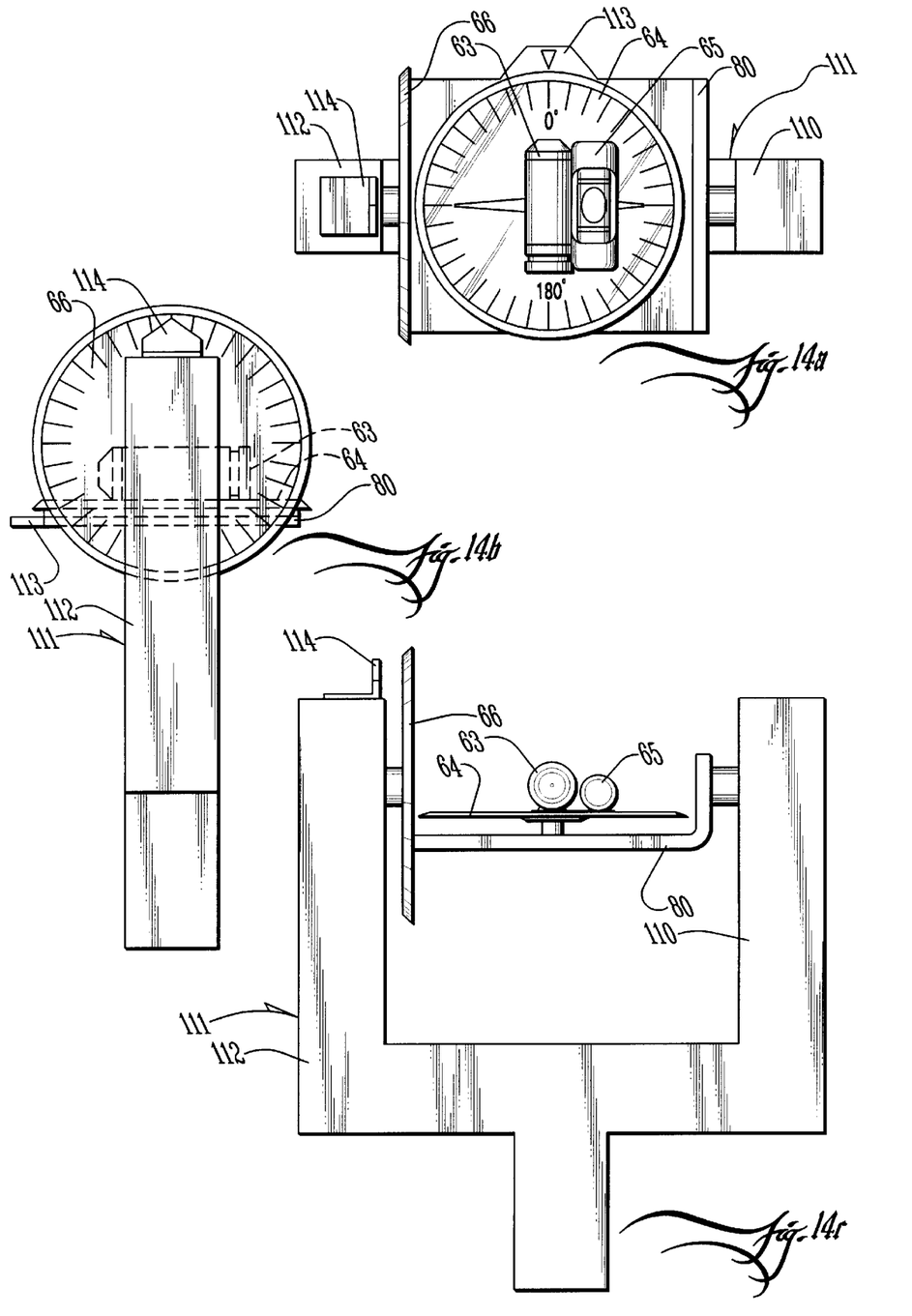
FIG. 14a is a plan view of an alternative embodiment of the stereotactic assembly.
FIG. 14b is a left side elevation view of an alternative embodiment of the stereotactic assembly.
FIG. 14c is a front elevation view of an alternative embodiment of the stereotactic assembly.

A vertical adjustment mechanism for the stereotactic assembly 50 is described above with reference to FIG. 4. An alternative mechanism may be described with reference to FIGS. 13a and 13b in which the vertical tube 55 and glide 56 are replaced with a first member 100 with an elongated dovetail 101 and a second member 103 with a dovetail shaped slot 104 in which the dovetail 101 is slidingly received. The vertical position of the first member 100 with respect to the second member 103 may be fixed with a set screw 105 which is threadedly received in a threaded hole 106 in the second member 103 so that the set screw 105 engages the dovetail 101, thereby preventing the first member 100 from vertical movement with respect to the second member 103. Either the first member 100 or the second member 103 may be attached to the fold down leaf 12 by means of the bolts 102, 107, while the other set of bolts attaches to the stereotactic assembly 50.

As described above with respect to FIG. 7, the horizontal position of the laser 63 may be set by moving a rod 81 with respect to vertical supports 62. An alternative version is described with respect to FIGS. 14a, b, and c as follows in which the patient platform is moved to set the horizontal position of the laser 63. In this embodiment, the horizontal protractor 64 is mounted for rotation on the turntable support 80, which is in turn affixed to the vertical protractor 66. The laser 63 is mounted on the horizontal protractor 64 so that the centerline of the laser 63 is in the same plane as the center of rotation of the vertical protractor 66. A bubble level 65 is likewise mounted to the horizontal protractor 64. The entire assembly comprising the vertical protractor 66, the horizontal protractor 64 and the turntable support 80 is mounted for rotation between the arms 110, 112 of a yoke 111. The yoke 111 is mounted to the table 58. The turntable support 80 may be provided with a horizontal reference pointer 113 and the left arm 112 of the yoke 111 provided with a vertical reference pointer 114 for assisting in setting the horizontal angle on the horizontal protractor 64 and the vertical angle on the vertical protractor 66, respectively.

The present invention must be constructed of non-magnetic material since it is located on the fringes on the very powerful MRI field. Suitable materials include stainless steel, aluminum or acrylic.

The present invention has been described with reference to certain preferred and alternative embodiments that are intended to be exemplary only and not limiting to the full scope of the present invention as set forth in the appended claims.

What is claimed is:

1. A combination of a stereotactic apparatus and an imaging device for guiding a medical instrument from a selected entry point on a body of a patient to a selected target mass within the body of the patient, comprising:

means for determining a horizontal angle between said entry point and said selected target mass;

means for determining a vertical angle between said entry point and said selected target mass;

a laser generating a guide beam and mounted to a horizontal protractor for rotation of said laser in a horizontal plane to align said laser with said horizontal angle;

a vertical protractor;

means for mounting said horizontal protractor to said vertical protractor for rotation in a vertical plane to align said laser with said vertical angle;

means for translating said horizontal protractor in a horizontal plane for aligning said guide beam with said selected entry point;

means for translating said vertical protractor in a vertical plane for aligning said guide beam with said selected entry point.

2. A method for use with an imaging device for guiding a medical instrument from a selected entry point on a body of a patient to a selected target mass within the body of the patient, comprising the steps of:

placing a reference target at said selected entry point;

determining a horizontal angle between said reference target and said selected target mass;

determining a vertical angle between said reference target and said selected target mass;

providing a laser generated guide beam aligning said laser generated guide beam with said horizontal angle;

aligning said laser generated guide beam with said vertical angle;

translating said laser in a horizontal plane and aligning said laser generated guide beam with said reference target;

translating said laser in a vertical plane and aligning said laser generated guide beam with said reference target;

removing said reference target from said selected entry point; and aligning said medical instrument with said laser generated guide beam so as to guide said medical instrument from said entry point to said target mass.

3. A stereotactic apparatus for use with an imaging device for guiding a medical instrument from a selected entry point on a body of a patient to a selected target mass within the body of the patient where a spatial relationship between the entry point and the target mass is defined by a horizontal angle from the entry point to the target mass and a vertical angle from the entry point to the target mass, comprising:

an assembly comprising a first protractor, a turntable support, a second protractor and a laser;

said first protractor being mounted on said turntable support for rotation about a first axis of rotation;

said second protractor being affixed to said turntable support, said second protractor and said turntable support together mounted for rotation about a second axis of rotation, said second axis of rotation being horizontal and said first axis of rotation being always perpendicular to said second axis of rotation;

said laser being affixed to said first protractor; said laser generating a guide beam along a third axis; said third axis being always perpendicular to said first axis of rotation and further being in a plane which always includes said second axis of rotation;

means for relative horizontal movement between said assembly and the entry point on the patient for aligning said guide beam with the entry point along the horizontal angle;

a vertical slide operatively attached to said assembly whereby said assembly may be translated vertically for aligning said guide beam with the entry point along the vertical angle.

4. The stereotactic apparatus of claim 3 wherein said means for relative horizontal movement comprises a rod mounted for horizontal sliding movement and rotational movement in a pair of vertical supports, said assembly being affixed to said rod in an offset fashion whereby said third axis of said guide beam of said laser is in the same plane as the axis of rotation of rod.

5. The stereotactic apparatus of claim 3 further comprises a yoke for mounting said assembly for rotation about said second axis of rotation.

\* \* \* \* \*